(12) United States Patent
Hayes et al.

(10) Patent No.: US 7,064,104 B2
(45) Date of Patent: Jun. 20, 2006

(54) METHODS OF MANAGING THE SYMPTOMS OF PREMENSTRUAL SYNDROME

(75) Inventors: Bruce Leslie Hayes, Colerain Township, OH (US); Alice Lyles Burkes, Forest Park, OH (US); Mary Lynn Stoeckle, Green Township, OH (US); Donald Lee Hughes, East Westwood, OH (US); Carl Gordon Kindberg, West Chester Township, OH (US); Denise Jean Bien, Mt. Lookout, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/461,650

(22) Filed: Jun. 13, 2003

(65) Prior Publication Data

US 2004/0254122 A1    Dec. 16, 2004

(51) Int. Cl.
*A61K 31/70*     (2006.01)
*A61K 38/00*     (2006.01)

(52) U.S. Cl. .............................. 514/2; 514/23; 514/54; 514/419

(58) Field of Classification Search .................... 514/2, 514/23, 54, 419
See application file for complete search history.

(56) References Cited

U.S. PATENT DOCUMENTS

| 4,210,637 A | 7/1980 | Wurtman |
| 4,381,121 A | 4/1983 | Hanley |
| 4,946,679 A | 8/1990 | Thys-Jacobs |
| 5,606,535 A | 2/1997 | Lynn |
| 5,612,320 A | 3/1997 | Wurtman |
| 5,691,324 A | 11/1997 | Sandyk |
| 5,760,014 A | 6/1998 | Wurtman |
| 6,022,323 A | 2/2000 | Jackson |
| 6,174,542 B1 | 1/2001 | Hinton et al. |
| 2002/0192310 A1 | 12/2002 | Bland et al. |
| 2003/0190381 A1 | 10/2003 | Bland et al. |
| 2004/0220118 A1 | 11/2004 | Bland et al. |
| 2005/0226949 A1 | 10/2005 | Bland et al. |
| 2006/0034954 A1 | 2/2006 | Bland et al. |

FOREIGN PATENT DOCUMENTS

| EP | 2 138 571 A1 | 1/2000 |
| WO | WO 99/55174 A1 | 11/1999 |

OTHER PUBLICATIONS

Dose-Dependent Effect of a x-Lactalbumin in Combination with Two Different Doses of Glucose on the Plasma Trp/LNAA Ratio—C.R. MARCUS—Nutrition Neuroscience, vol. 3, pp. 345-355.

The Effect of a Carbohydrate-Rich Beverage on Mod, Appetite, and Cognitive Function in Women with Premenstrual Syndrome—Raja Sayegh—Obstetrics & Gynecology, vol. 86, No. 4, Part 1, Oct. 95, pp. 50-528.

Whey Protein Rich in x-Lactalbumin Increases the Ratio of Plasma Tryptophan to the Sum of the Other Large Neutral Amino Acids and Improves Cognitive Performance in Stress-Vulnerable Subjects—C. Rob Marcus—Am J Clin Nutr 2002; 75 pp. 1051-1056.

Meal Composition and Plasma Amino Acid Ratios: effect of Various Proteins or Carbohydrates, and of Various Protein Concentrations—Hidehiko Yokogoshi—Metabolism, vol. 35, No. 9 (Sep.) 1986, pp. 837-842.

PCT International Search Report dated Nov. 11, 2004.

*Primary Examiner*—Elli Peselev
(74) *Attorney, Agent, or Firm*—Bridget Ammons Murray; Kevin C. Johnson; David M. Weirich

(57) ABSTRACT

Methods of increasing the tryptophan:LNAA ratio in blood of an individual are taught. Such methods are useful in managing conditions such as premenstrual syndrome, perimenopause, menopause, seasonal affective disorder, stress, or depression. The methods include orally administering specific doses of a carbohydrate blend combined with high tryptophan containing proteins.

11 Claims, No Drawings

METHODS OF MANAGING THE SYMPTOMS OF PREMENSTRUAL SYNDROME

FIELD OF THE INVENTION

This invention relates to methods of increasing the tryptophan:LNAA ratio in blood of an individual. Such methods are useful in managing conditions such as premenstrual syndrome, perimenopause, menopause, seasonal affective disorder, stress, or depression.

BACKGROUND OF THE INVENTION

Serotonin is a neurotransmitter largely responsible for emotional response and believed, by the inventors, to play a key role in the transmission of pain impulses from the source of the pain to the brain. As such, conditions such as PMS, perimenopause, menopause/post-menopause, seasonal affective disorder, stress, and depression may be aggravated when the brain experiences a serotonin deficiency. Tryptophan is a precursor to serotonin and it competes with other large neutral amino acids (LNAA) for transport into the brain. Thus, others have attempted to increase brain serotonin by raising the ratio of tryptophan to LNAA in the blood through various mechanisms.

One mechanism taught in the prior art uses an insulin response, such as is triggered by the consumption of carbohydrates. Literature suggests that this mechanism works best when protein is absent and/or at low levels. For example, one published study states "As little as 2–4% of the calories of a meal as protein will prevent an increased availability of tryptophan", Benton, D. & Donohoe, R. T, "The Effects of Nutrients on Mood", *Public Health Nutrition*, Vol. 2(3a), pp. 403–409 (1999). The insulin response encourages some portion of LNAA to leave the blood stream and enter skeletal muscle. Tryptophan is more resistant than the other LNAA to entering skeletal muscle, with proportionally more staying in the blood. The result is a relatively higher ratio of tryptophan:LNAA in the blood.

The second mechanism for increasing the tryptophan:LNAA ratio is to tailor diets to comprise proteins that are rich in tryptophan relative to other LNAA, with the idea that as the relative amount of tryptophan available in the protein goes up, the tryptophan:LNAA ratio in the blood will also go up. One study dosed a high tryptophan containing whey protein with carbohydrate (orange juice) and either 25 or 50 g of glucose, Markus, C. R. et al., "Dose-Dependent Effect of α-Lactalbumin in Combination with Two Different Doses of Glucose on the Plasma Trp/LNAA Ratio", *Nutritional Neuroscience*, Vol. 3, pp. 345–355 (2000). The study concluded that the different glucose doses did not influence the tryptophan:LNAA ratio. The study also concluded that "since insulin responses across time did not significantly differ between the different α-lactalbumin conditions differences in the time dependent effects between these α-lactalbumin conditions on plasma Trp/LNAA do not seem to depend on insulin alterations" (page 353).

Notwithstanding these teachings, it has been surprisingly found that the use of both mechanisms together actually enhances the effectiveness in raising the tryptophan:LNAA ratio in blood. The inventors of the current invention have discovered a dosage regimen that provides a tryptophan:LNAA ratio boost when relatively low levels of carbohydrates and a high tryptophan containing protein are administered.

BACKGROUND ART

WO 99/55174 A1, Regnault et al., relates to PROTEIN SUPPLEMENT, FOOD COMPOSITION CONTAINING IT, THEIR PROCESS OF PREPARATION AND USE.

U.S. Pat. No. 5,612,320, Wurtman et al., relates to THERAPEUTIC CARBOHYDRATE BLENDS FOR TREATING AND AIDING PREMENSTRUAL SYNDROME.

SUMMARY OF THE INVENTION

This invention relates to a method of increasing the tryptophan:LNAA ratio in blood of an individual, comprising orally administering to the individual a carbohydrate blend and a high tryptophan containing protein.

DETAILED DESCRIPTION OF THE INVENTION

The term "tryptophan" or "Trp" refers to the neutral amino acid that is a precursor to serotonin.

The phrase "large neutral amino acids" or "LNAA" generally refer to neutral amino acids that compete for transport across the blood brain barrier using a specific amino acid transport mechanism. The LNAA include tryptophan, tyrosine, valine, isoleucine, leucine, and phenylalanine.

The phrases "tryptophan:LNAA ratio", "tryptophan and LNAA in a ratio of", "Trp/LNAA", or the like, as used herein, refer to the weight ratio of tryptophan to the large neutral amino acids tyrosine, valine, isoleucine, leucine, and phenylalanine.

"PMS" or "premenstrual syndrome" refers to physical and emotional symptoms experienced by women during the luteal phase of their menstrual cycle, typically in the days immediately before the onset of menstruation.

"Physical symptoms" refers to physical symptoms of PMS including but not limited to PMS-related pain (such as backache, headache, generalized aches and pains), breast tenderness, bloating, and cramping (such as in the abdomen).

"Emotional symptoms" refers to emotional symptoms of PMS including but not limited to irritability and mood swings/changes.

The phrase "managing PMS" means that a reduction in severity of PMS symptoms.

The phrase "other indications" includes but is not limited to perimenopause, menopause/post-menopause, seasonal affective disorder, stress, or depression.

"Perimenopause" or "perimenopausal" refers to the physical and emotional symptoms associated with the phase prior to the onset of menopause. During this period the woman's regular menstrual cycle length gradually decreases as a result of a shortened duration of the follicular phase. Her menses changes, often abruptly, to a pattern of irregularity with increasing periods of amenorrhea. The physical and emotional symptoms associated with PMS are often exacerbated during this phase prior to the onset of menopause.

"Amenorrhea" refers to the absence or suppression of menstruation.

"Menopause" or "menopausal" refers to the period that marks the permanent cessation of menstrual activity.

"Post-menopause" refers to the period after the cessation of menstrual activity. During this period, emotional symptoms such as anxiety, depression, irritability, and fatigue increase. Physical symptoms include worsening tension headaches and joint/muscle pain.

"Seasonal Affective Disorder" or "SAD" refers to a mood disorder characterized by depression related to certain seasons of the year, especially winter.

"Stress" or "stressed" refers to the negative "wear and tear" the body experiences as an individual adjusts to a continually changing environment. Stress has physical and emotional effects that may result in feelings of distrust, rejection, anger, or depression. These negative feelings may lead to physical symptoms of headaches, upset stomach, insomnia, ulcers, high blood pressure, rashes, or heart disease.

"Depression" refers to a state of having an altered mood, feeling low in spirit, dejected, and/or having a decreased level of interest in food, sex, work, friends, family, hobbies, or entertainment.

The term "protein" refers to natural and synthetic polymers of amino acids suitable for use in a food product. These include, but are not limited to, proteins, polypeptides (down to two amino acids), protein isolates, and protein hydrolysates from natural, semisynthetic, or synthetic sources.

The phrase "single dosage form" means that the composition is to be consumed in one sitting, as a supplement to the diet normally eaten by the individual. For example, this single dosage form includes, but is not limited to, forms such as a powdered or a pre-made beverage, a chew, a bar, a wafer, a pudding, a syrup or elixir, capsule, sublingual tab, a shot, a transdermal patch, or even a pill. Additionally, the phrase "single dosage form" contemplates that the protein supplement may be physically separated from the carbohydrate blend, e.g. a carbohydrate blend bar and a protein shake drink.

As used herein the symbols "g" is grams, "kg" is kilogram. "kg/m$^2$" is kilograms per meter squared.

I. Compositions Useful in the Methods of the Current Invention

The current invention involves administering tryptophan in the form of a high tryptophan containing protein in combination with a carbohydrate blend. Such doses should be taken as single dosage forms on an "as needed basis", with additional doses over time as the symptoms return.

a. High Tryptophan Containing Proteins

The ratio of tryptophan to other LNAA is more important to the current invention than the absolute level of tryptophan. Further, the ratio of amino acids in proteins is highly variable. This invention calls for high tryptophan containing proteins, which are those proteins which comprise tryptophan and LNAA in a weight ratio of at least about 0.06:1 The phrase "high tryptophan containing proteins" also includes pure protein isolates of tryptophan. For example, one useful supply of tryptophan is Vivinal$^R$ ALPHA from Borculo Domo, The Netherlands, which has a weight tryptophan:LNAA ratio of 0.09:1. Another useful source is BioPURE Alphalactalbumin™ from Davisco Foods International, Inc., which has a weight tryptophan:LNAA ratio of 0.16:1.

In determining how much of a particular high tryptophan containing protein to dose, one needs to consider the protein source, or more particularly, the amount of tryptophan contained by the protein. The amount of tryptophan needed to provide the benefits of increasing the tryptophan:LNAA ratio in the blood may be varied depending on the dosing of the carbohydrate blend as discussed further below. For instance, while the desired benefits may be realized by dosing as much as a gram, or even more, of tryptophan, it has been discovered that a dose of lower amounts of tryptophan (in the form of high tryptophan containing proteins) than disclosed in the prior art can be used when the high tryptophan containing proteins are dosed in combination with a carbohydrate blend. Specifically, the desired increase in the tryptophan:LNAA ratio in blood of an individual can be realized by dosing an individual with an amount from about 0.15 g to about 0.40 g of tryptophan. It is believed that the desired tryptophan:LNAA ratio in the blood of the individual can be realized by dosing a relatively small amount of tryptophan, in some embodiments about 0.25 g of tryptophan, due the synergistic effect of combining high tryptophan containing proteins with carbohydrates. This dosing regimen allows for high tryptophan containing proteins to be utilized in a more cost effective manner than previously realized. The equation below explains how to calculate the grams of tryptophan delivered, depending upon the protein source.

$$g\, Trp = gSource \times \frac{gProtein}{gSource} \times \frac{gTrp}{gProtein}$$

where: g Trp=g tryptophan delivered g Source=g protein source raw material $$\frac{gProtein}{gSource} = \text{amount of protein in the raw material}$$

$$\frac{gTrp}{gProtein} = \text{amount of tryptophan in the protein}$$

Alternatively, one can calculate the grams of tryptophan delivered if one knows the amount of tryptophan in the source raw material by the following equation:

$$gTrp = gSource \times \frac{gTrp}{gSource}$$

where: g Trp=g tryptophan delivered g Source=g protein source raw material $$\frac{gTrp}{gSource} = \text{amount of tryptophan in the source raw material}$$

b. Carbohydrate Blend

The carbohydrate blends useful in the current invention refer to rapidly digestible carbohydrates that facilitate the necessary insulin response. For example, components of the carbohydrate blend could include, but are not limited to, dextrose, dextrin, maltodextrin, starch, and modified starches. In some embodiments, the carbohydrate blend may comprise dextrose and maltodextrin in a weight ratio of 70 to 30. The carbohydrate blends are typically administered from at least about 20 g, alternatively from about 30 g to about 40 g in a single dosage form. Dosing more than 40 g of carbohydrate would not thwart the effectiveness of the combination, but is not necessary and adds caloric content with little/no additional benefit in raising tryptophan:LNAA ratio in the blood of the user.

II. Optional Components

The compositions of the current invention can optionally comprise other ingredients to aid in managing PMS or to provide an additional benefit (such as nutrition, weight management, etc.). Other ingredients may include but are not limited to magnesium, iron, calcium, vitamin B-6, niacin, Thiamine, Vitamin B-12, Agnus Castus Vitex, Vitamin D, Vitamin E, Vitamin C, Chromium, Selenium, Zinc, Folic Acid, Theanine, Evening Primrose Oil, Omega-3 Fatty Acids, and other botanical, vitamin, or mineral ingredients.

III. Method of Making the Compositions Useful in the Current Invention

Making the compositions is well known to those skilled in the art. Each of the components is available in dry form and can be accurately weighed out. If the product is to be delivered as a dry powder, the ingredients can be weighed out and added to a single dosage form packet without the need for mixing. If done in larger batches, the pre-weighed ingredients will need to be mixed until homogeneous as in a ribbon blender before packets are filled to the correct weight to provide the desired dose of each ingredient in an individual packet. Such powdered packets can later be reconstituted in water and consumed, e.g. within 10 minutes.

IV. Examples of the Current Invention

Protocol for Blood Draw Clinical

Seventy-two, healthy adult female subjects with a BMI (Body Mass Index—$kg/m^2$) of 20–27 and with a regular menstrual cycle were entered into the study. The study was a randomized, controlled, blind clinical study involving four nutritional supplement drinks that were tested for their effect on plasma tryptophan:LNAA ratio. Each subject received two of the four drinks. Drinks were taken between day 4 and 12 of their menstrual cycle. Subjects had a five-day interval between test drinks.

On the test day, research site staff mixed each dose with 8 ounces of water. Each dose was consumed within a five-minute period in the presence of a member of the research staff. Blood draws for amino acids were taken immediately before dosing (Time 0) and at 60, 90, 120, and 180 minutes post-dose.

Compositional Information

Compositions A, B, C, and D were formulated to be isocaloric.

Composition A is a blend of the current invention, including 38.6 g of carbohydrates (27.0 g of dextrose and 11.6 g of maltodextrin) plus 10.0 g of alphalactalbumin enriched whey protein (Vivinal$^R$ ALPHA, a high tryptophan containing protein). Protein contributes 0.16 g of tryptophan per dose.

Composition B is the placebo control product, including 32.5 g of carbohydrate (all dextrose) and 16.3 g of calcium caseinate, a typical protein.

Composition C is a carbohydrate blend without the addition of any protein and includes 47.5 g of carbohydrate (33.3 g dextrose and 14.2 g of maltodextrin).

Composition D is a different carbohydrate blend, also without the addition of any protein and includes 48.7 g of carbohydrates (31.9 g of dextrose, 13.7 g maltodextrin and 3.1 g potato starch).

Results of the Blood Draw Clinical

The product of the current invention (A) was significantly more effective at increasing the tryptophan:LNAA ratio than was either of the carbohydrate blends or the protein control.

- The "overall" interval reflects a combination of all time points after time 0 and indicates that the product of the current invention (A) raised the tryptophan:LNAA ratio to a significantly higher level than did either of the other test products or the protein control over the duration studied.
- At specific times points, 60 and 120, the product of the current invention (A) raised the tryptophan:LNAA ratio to a significantly higher level than did either of the other test products or the protein control.
- The product of the current invention (A) was the only product tested that increased the tryptophan:LNAA ratio significantly higher than baseline for all four time intervals.

Summary Statistics for Trypotophan:LNAA Ratio – % of Baseline

| | Example of the Current Invention High Tryptophan Protein + Carbohydrates (A) | | | Comparative Examples | | | | | | | | |
|---|---|---|---|---|---|---|---|---|---|---|---|---|
| | | | | Protein (Casein) Control (B) | | | Carbohydrate Blend (C) | | | Carbohydrate Blend (D) | | |
| (min) | N | % Baseline | Sig | N | % Baseline | Sig | N | % Baseline | Sig | N | % Baseline | Sig |
| 0 | 34 | 100 | | 35 | 100 | | 38 | 100 | | 40 | 100 | |
| 60 | 32 | 119.7 ± 3.2* | BCD | 35 | 93.6 ± 3.0* | | 36 | 109.7 ± 3.0* | B | 37 | 105.7 ± 2.9 | B |
| 90 | 27 | 118.6 ± 3.7* | B | 28 | 88.6 ± 3.6* | | 31 | 111.2 ± 3.4* | B | 33 | 112.7 ± 3.3* | B |
| 120 | 23 | 132.0 ± 4.1* | BCD | 21 | 83.7 ± 4.3* | | 28 | 120.6 ± 3.7* | B | 30 | 121.0 ± 3.6* | B |
| 180 | 22 | 113.4 ± 4.0* | B | 15 | 79.6 ± 4.8* | | 22 | 107.2 ± 4.0 | B | 26 | 116.4 ± 3.7* | BC |
| Overall | 22 | 121.1 ± 2.1 | BCD | 15 | 88.3 ± 2.2 | | 22 | 111.3 ± 2.0 | B | 26 | 113.9 ± 2.0 | B |

Results are Mean ± Standard Error
*indicates significant difference at the 5% level from baseline (i.e., time 0) using t-test/Wilcoxon text.
Upper case letter indicates a significant difference at the 5% level between columns. Parametric analysis of covariance (baseline included as covariant) was used to compare treatments at all time points. Overall comparisons are based on repeated measures analysis of variance.

Other Compositions of the Current Invention

Composition E is a blend of the current invention, including 34.0 g carbohydrates (22.3 g of dextrose, 9.6 g of inaltodextrin, and 2.1 g potato starch) plus 4.0 g of alphalactalbumin enriched whey protein (Davisco BioPURE—Alphalactalbumin™, a high tryptophan containing protein). Protein would contribute 0.19 g of tryptophan per dose.

Composition F is a blend of the current invention, including 34.0 g carbohydrates (22.3 g of dextrose, 9.6 g of maltodextrin, and 2.1 g potato starch) plus 8.0 g of alpha-lactalbumin enriched whey protein (Davisco BioPURE—Alphalactalbumin™, a high tryptophan containing protein). Protein would contribute 0.38 g of tryptophan per dose.

All documents cited in the Detailed Description of the Invention are, in relevant part, incorporated herein by reference; the citation of any document is not to be construed as an admission that it is prior art with respect to the current invention.

While particular embodiments of the current invention have been illustrated and described, it would be obvious to those skilled in the art that various other changes and modifications can be made without departing from the spirit and scope of the invention.

What is claimed is:

1. A method of increasing the tryptophan:LNAA ratio in blood of an individual, comprising orally administering to the individual a composition comprising a rapidly digestible carbohydrate blend; said rapidly digestible carbohydrate blend in the amount of no more than about 40 g; and a high tryptophan containing protein which comprises tryptophan, said high tryptophan containing protein being in the amount of from about 4 g to about 10 g; wherein the high tryptophan containing protein contributes no more than about 0.25 g of tryptophan per dose; wherein said composition is administered as a single dosage form creating an increase of the tryptophan:LNAA ratio in blood of the individual above a baseline at 60 minutes after administration.

2. A method according to claim 1 wherein increasing the tryptophan:LNAA ratio in blood is intended to manage an individual's PMS.

3. A method according to claim 2 wherein said high tryptophan containing protein comprises at least about 0.16 g of tryptophan.

4. A method according to claim 2 wherein said individual's PMS comprises PMS-related pain.

5. A method of increasing a tryptophan:LNAA ratio in the blood of an individual, comprising orally administering to the individual a composition comprising from about 4 g to about 10 g of a high tryptophan containing protein wherein the high tryptophan containing protein contributes from about 0.15 g to about 0.40 g of tryptophan per dose and no more than about 40 g of a rapidly digestible carbohydrate blend per dose wherein said composition is administered as a single dosage form creating an increase of the trypophan:LNAA ratio in blood of the individual above a baseline at 60 minutes after administration.

6. A method according to claim 5 wherein increasing the tryptophan:LNAA ratio in the blood is intended to manage an individual's PMS.

7. A method according to claim 6 wherein said individual's PMS comprises PMS related pain.

8. A method according to claim 6 wherein increasing the tryptophan: LNAA ratio in the blood is intended to manage the individual's emotional symptoms.

9. A kit for use in managing PMS comprising:
   a. instructions for using a composition contained therein for managing PMS; and
   b. a composition which comprises from about 4 g to about 10 g of a high tryptophan containing protein, wherein the high tryptophan containing protein contributes from about 0.15 g to about 0.40 g of tryptophan per dose, and no more than about 40 g of a rapidly digestible carbohydrate blend; wherein said composition is administered in a single dosage form creating an increase of the tryptophan:LNAA ratio in blood of an individual above a baseline at 60 minutes after administration.

10. A kit according to claim 9 wherein the composition further comprises from about 25 g to about 40 g of a carbohydrate blend.

11. A kit according to claim 9 wherein the high tryptophan containing protein contributes no more than about 0.25 g of tryptophan per dose.

* * * * *